(12) United States Patent
Croizet-Berger et al.

(10) Patent No.: US 11,427,476 B2
(45) Date of Patent: Aug. 30, 2022

(54) MESOPOROUS SILICAS AND METHOD FOR THE SYNTHESIS THEREOF

(71) Applicant: Sil'innov S.c.r.l., Courcelles (BE)

(72) Inventors: Karine Croizet-Berger, Court St Etienne (BE); Maxime Delmeule, Courcelles (BE); Julien Estager, Kontich (BE); Nicolas Mannu, Waterloo (BE); Benoit Kartheuser, Ciney (BE)

(73) Assignee: Sil'Innov S.c.r.l., Courcelles (BE)

( * ) Notice: Subject to any disclaimer, the term of this patent is extended or adjusted under 35 U.S.C. 154(b) by 933 days.

(21) Appl. No.: 16/095,398

(22) PCT Filed: Mar. 29, 2017

(86) PCT No.: PCT/EP2017/057427
§ 371 (c)(1),
(2) Date: Oct. 22, 2018

(87) PCT Pub. No.: WO2017/182245
PCT Pub. Date: Oct. 26, 2017

(65) Prior Publication Data
US 2019/0084836 A1   Mar. 21, 2019

(30) Foreign Application Priority Data
Apr. 22, 2016   (BE) .................................. 2016/5280

(51) Int. Cl.
*C01B 33/193*   (2006.01)
*A23L 33/16*   (2016.01)
(Continued)

(52) U.S. Cl.
CPC .......... *C01B 33/193* (2013.01); *A23L 29/015* (2016.08); *A23L 33/16* (2016.08);
(Continued)

(58) Field of Classification Search
CPC ... C01B 33/193; C01B 33/18; C01P 2006/12; C01P 2006/14; C01P 2006/16;
(Continued)

(56) References Cited

U.S. PATENT DOCUMENTS

2011/0268970 A1* 11/2011 Ying .................... A61P 9/12
428/402
2015/0374018 A1   12/2015 Normand

FOREIGN PATENT DOCUMENTS

EP   2256088 A1   12/2010

OTHER PUBLICATIONS

JP2017081789, application filed date: Oct. 2015, see machine translation.*
(Continued)

*Primary Examiner* — Smita S Patel
(74) *Attorney, Agent, or Firm* — James Creighton Wray; Cermak Nakajima & McGowan LLP

(57) ABSTRACT

The present invention provides a mesoporous silica comprising of components A and B such that component A is a surfactant of a saponin family and component B is a precursor of a silica. The present inventions also provides a method of producing said mesoporous silica by mixing components A and B in a solvent.

17 Claims, 5 Drawing Sheets

(51) Int. Cl.
| | |
|---|---|
| *C01B 33/18* | (2006.01) |
| *A61K 8/25* | (2006.01) |
| *A23L 29/00* | (2016.01) |
| *A61Q 19/00* | (2006.01) |
| *A61K 8/02* | (2006.01) |
| *A61K 8/60* | (2006.01) |

(52) U.S. Cl.
CPC .............. *A61K 8/0279* (2013.01); *A61K 8/25* (2013.01); *A61K 8/602* (2013.01); *A61Q 19/00* (2013.01); *C01B 33/18* (2013.01); *A61K 2800/10* (2013.01); *A61K 2800/413* (2013.01); *C01P 2004/03* (2013.01); *C01P 2006/12* (2013.01); *C01P 2006/14* (2013.01); *C01P 2006/16* (2013.01)

(58) Field of Classification Search
CPC ............. C01P 2004/03; A61K 2800/10; A61K 2800/413; A61K 8/0279; A61K 8/25; A61K 8/602; A61Q 19/00
See application file for complete search history.

(56) References Cited

OTHER PUBLICATIONS

Bérubé et al.; "Calcination and Thermal Degradation Mechanisms of Triblock Copolymer template in SBA-15 Materials", ScienceDirect, Dec. 5, 2007, pp. 469-479.

Brigante et al.; "Biotemplated Synthesis of Mesoporous Silica for Doxycycline Removal. Effect of pH, Temperature, Ionic Strength and Ca2+ Concentration on the Adsorption Behaviour", Microporous and Mesoporous Materials, vol. 225, Feb. 3, 2016, pp. 534-542.

Dai et al. "A Green Process for the Synthesis of Controllable Mesoporous Silica Materials", Microporous and Mesoporous Materials, Elsevier Science Publishing, New York, US, vol. 147, No. 1, Jun. 25, 2011, pp. 281-285.

Geethalakshmi et al.; "Characterization and Antimicrobial Activity of Gold and Silver Nanoparticles Synthesized Using Saponin Isolate from Trianthema Decandra L", Industrial Crops and Productcs, vol. 51, Aug. 17, 2013, pp. 107-115.

Huang et al., "Effect of the Polar Modifiers on Supercritical Extraction Efficiency for Template Removal from Hexagonal Mesoporous Silica Materials: Solubility Parameter and Polarity Considerations", Separation and Purification Technology, 118, Jan. 31, 2013, pp. 120-126.

Standar et al.; "Alkl-Glycoside Surfactants in the Synthetis of Mesoporous Silica Films", Silicon Chemistry, Kluwer Academis Publishers, DO, vol. 2, No. 3-4, Aug. 15, 2003, pp. 157i-165.

Tanev et al.; "Misoporous Silica Molecular Sieves Prepared by Ionic and Neutral Surfactant Templating: A Comparison of Physical Properties", Chem. Mater, 1996, pp. 2068-2079.

Waldron et al.; "Formation of Monodisperse Mesoporous Silica Microparticles via Spray-Drying", Journal of Colloid and Interface Science, Academic Press, New York, NY, US, vol. 418, Dec. 19, 2013, pp. 225-233.

Zhuang et al.; "An Alternative Method to Remove PEO-PPO-PEO Template in Organic-Inorganic Mesoporous Nanocomposites by Sulfuric Acid Extraction", Applied Surface Science, 2010, pp. 5343-5348.

* cited by examiner

MESOPOROUS SILICAS AND METHOD FOR THE SYNTHESIS THEREOF

This application claims the benefit of Belgian Application No. 2016/5280 filed Apr. 22, 2016 and PCT/EP2017/057427 filed Mar. 29, 2017, International Publication No. WO 2017/182245 A1, which are hereby incorporated by reference in their entirety as if fully set forth herein.

FIELD OF THE INVENTION

The present invention relates to a mesoporous silica and a method of producing said silica. The process and the silica are characterized by the use of natural compounds belonging to the family of saponins as structuring agent.

STATE OF THE ART

Thanks to their high surface area, porous materials, especially mesoporous silicas, are of major interest in fields as diverse as catalysis, electronics, semiconductors and composite materials and are also an irreplaceable tool today, in the biological and medical fields.

The mechanism of synthesis of organized mesoporous silica materials is well known. This mechanism, known as the Cooperative Templating Mechanism (CTM), proposes that the addition of a silica precursor leads, by interaction with the aggregates formed by a surfactant, to the formation of an organic/inorganic hybrid organized phase. This mechanism is therefore based on a self-assembly between the surfactant molecules and the inorganic precursor that leads to an organization of the system. There is a wide range of surfactants that can be used as structuring agents in mesoporous silica synthesis processes. They can be anionic, cationic or neutral.

Whatever the synthetic processes used, the surfactants are in any case of non-natural origin. These are petroleum-based molecules that must be extracted from the final material in order, on the one hand, to allow subsequent use in medical, biological or pharmaceutical applications and, on the other hand, to release the porosity. EP 2256088 uses a calcination process to extract the surfactant molecules. This process, in addition to being energy-consuming, destroys the surfactant used which, if it is expensive, can not enter a recycling process. Calcination also has the disadvantage of modifying the physicochemical properties of the mesoporous materials. This process decreases, for example, the mesh parameter (Bérubé and Kaliaguine. *Micropor Mesopor Mat.* 2008, 115:469-479). On the other hand, the exothermic nature of the process increases the defects present in the inorganic structure.

There are other techniques for extracting the surfactant from the mesoporous material. A sulfuric acid extraction process described by Zhuang, Quian and Wan in *Applied Surface Science*, 2010, 256; 5343-5348 "An alternative method to remove PEO-PPO-PEO template in organic-inorganic mesoporous nanocomposites by sulfuric acid extraction". This process has the disadvantage of altering the surfactant which can no longer be recycled. In addition, this technique requires the establishment of a heavy and expensive system for recycling the acid.

The work of Tanev and Pinnavaia (*Mater* 1996, 8 (8): 2068-2079) describes a method for extracting the surfactant by solvent. Extraction is facilitated when the surfactant is nonionic. Although this method has the advantage of allowing the recycling of the surfactant, the removal thereof from the porous material remains incomplete. This process is therefore generally coupled with calcination which makes it possible to completely release the porosity of the synthesized material.

Finally, Huang, Xu, and Li (*Separation and Purification Technology*, 118, 120-126 "Effect of the polar modifiers on supercritical extraction efficiency for hexagonal mesoporous silica materials: solubility parameter and polarity considerations") show that a supercritical fluid can make it possible to extract the surfactant from the mesoporous material. If this method effectively removes the surfactant and keep it intact, its implementation at the industrial level is complicated.

The mesoporous silicas of the prior art must therefore be subjected to a process which allows the removal of the surfactant. This process is quite complicated, energy intensive and expensive. There is thus a need for a mesoporous silica synthesis process and a mesoporous silica in which the removal of the surfactant could be avoided and/or facilitated and/or inexpensive.

The present invention aims to provide a solution to at least one of the problems mentioned above. The invention provides a process for the synthesis of mesoporous silica and a mesoporous silica obtained by the process. The process and the silica are as described in the claims.

SUMMARY OF THE INVENTION

In a first aspect, the present invention provides a mesoporous silica prepared by mixing components A and B such that A is a surfactant of the saponin family and B is a precursor of silica.

The silica precursor is represented by the formula Si(OR1)(OR2)(OR3)(OR4) in which R1, R2, R3 and R4 are independently chosen from hydroxyl, alkyl, glycols and trimethyl-1,2,3,4 groups, tetrahydronaphthalen, 1,1,1,3,3,3-hexafluoropropan-2-yl, dimethylsilyl, trimethylsilyl, ethoxysilyl, tributoxysilyl, diethoxy(methoxy)silyl, trimethoxysilyl, ethoxy(dimethoxy)silyl, butoxy(dipropoxy)silyl, tripropoxysilyl, diethoxy(trimethylsilyloxy)silyl, ethoxy-bis(trimethylsilyloxy)silyl, methyl-bis(trimethylsilyloxy)silyl, butoxy-bis(trimethylsilyloxy)silyl, diethoxy(triethoxysilyloxy)silyl, dimethyl(vinyl)silyl, trimethylsilyloxy, (3-methylpentoxy)silyl, 4,7,7-trimethyl-3-bicyclo[2.2.1]heptanyl, 2,2,4-trimethyl-3-bicyclo [2.2.1]heptanyl, propan-2-yloxy-bis(trimethylsilyloxy)silyl, dibutoxy(trimethylsilyloxy)silyl, trimethyl trimethoxysilyl, dibutoxy(ethenyl)silyl, diethyl bis (trimethylsilyl), (butan-2-yloxy)silyl, diacetyloxy-[(2-methylpropan-2-yl)oxy]silyl, acetyloxy(diethoxy)silyl, 4-(dimethylamino)phenyl, 4-(dimethylamino)phenyl, 2-(diethylamino)ethyl, pyridin-3-yl, 2-methylpropan-2-yl) oxy, 2,2,3,3,4,4,5,5,6,6,7,7-dodecafluoroheptyl, trichloro-2-ethylbutoxy, cyclononyl, 1-methoxypropan-2-yl, 2-(2-methoxyethoxy)ethyl, 2-butoxyethyl, 2-ethoxyethyl, 2-methoxyethyl, acetyl, acetyloxy(dipropoxy)silyl, 5-methyl-2-propan-2-ylcyclohexyl, butan-2-yloxy, methylphenyl, cyclohexyl, 2-aminoethyl, phenyl, prop-2-enyl, 2-fluoroethyl, acetate or trihydroxysilyloxy. The configuration R1=R2=R3=R4 is covered by the invention, or by the formula xSiO2:MyO where M is one or more metal atoms, one or more transition metal atoms, one or more non-metal atoms, a methylammonium, an actinide, y=1 or 2 or 3 or 4 and x is the SiO2/MyO molar ratio.

In a second aspect, the present invention provides a method of producing mesoporous silica in which components A and B are mixed in a solvent comprising water, such that A is a surfactant of the saponin family and B is a precursor silica compound represented by the formula Si(ORi)(OR2)(OR3)(OR4) wherein R1, R2, R3 and R4 are independently selected from hydroxyl, alkyl, glycols, trimethyl-1,2,3,4-tetrahydronaphthalen, 1,1,1,3,3,3-Hexafluoropropan-2-yl, dimethylsilyl, trimethylsilyl, ethoxysilyl, tributoxysilyl, diethoxy(methoxy)silyl, trimethoxysilyl, ethoxy (dimethoxy)silyl, butoxy(dipropoxy)silyl, tripropoxysilyl, diethoxy(trimethylsilyloxy)silyl, ethoxy-bis(trimethylsilyloxy)silyl, methylbis(trimethylsilyloxy)silyl, butoxy-bis(trimethylsilyloxy)silyl, diethoxy(triethoxysilyloxy)silyl, dimethyl(vinyl)silyl, trimethylsilyloxy, (3-methylpentoxy) silyl, 4,7,7-trimethyl-3-bicyclo[2.2.1]heptanyl, 2,2,4-trimethyl-3-bicyclo[2.2.1]heptanyl, propan-2-yloxy-bis(trimethylsilyloxy)silyl, dibutoxy(trimethylsilyloxy)silyl, trimethyl trimethoxysilyl, dibutoxy(ethenyl)silyl, diethyl bis(trimethylsilyl), (butan-2-yloxy)silyl, diacetyloxy-[(2-methylpropan-2-yl)oxy]silyl, acetyloxy(diethoxy)silyl, 4-(dimethylamino)phenyl, 4-(dimethylamino)phenyl, 2-(diethylamino) ethyl, pyridin-3-yl, 2-methylpropan-2-yl)oxy, 2,2,3,3,4,4,5,5,6,6,7,7-dodecafluoroheptyl, trichloro-2-ethylbutoxy, cyclononyl, 1-methoxypropan-2-yl, 2-(2-) methoxyethoxy) ethyl, 2-butoxyethyl, 2-ethoxyethyl, 2-methoxyethyl, acetyl, acetyloxy(dipropoxy)silyl, 5-methyl-2-propan-2-ylcyclohexyl, butan-2-yloxy, methylphenyl, cyclohexyl, 2-aminoethyl, phenyl, prop-2-enyl, 2-fluoroethyl, acetate, trihydroxysilyloxy. The configuration R1=R2=R3=R4 is covered by the invention, or by the formula xSiO2:MyO where M is one or more metal atoms, one or more transition metal atoms, one or more non-metal atoms, a methylammonium, an actinide, y=1 or 2 or 3 or 4 and x is the SiO2/MyO molar ratio.

The mesoporous silica of the invention can be used in the fields of human or animal nutrition, human or animal nutrition, the pharmaceutical industry, the cosmetic industry. The method and the silica of the invention have several advantages over the prior art silicas and their production methods. The method of the invention makes it possible to produce a silica comprising a natural and food-grade surfactant, in particular a surfactant belonging to the family of saponins. Silica comprising the natural surfactant can be used for various applications. The total removal of the surfactant is not necessarily required and its presence in the silica has no adverse effect on the various applications envisaged for the silica.

The fact that the silica can be used without total removal of the surfactant makes it possible (i) to maintain the properties of the silica and to avoid any alterations in the silica that may be caused by the treatments, in particular by calcination, aimed at removing the surfactant; (ii) significantly reduce the time and/or cost of preparing the silica; and (iii) preserve the environment by avoiding the use of chemicals or energy-consuming methods for the removal of the surfactant.

Maintaining the properties of the silica (point (i) above) makes it possible to guarantee the efficiency and the optimization of the applications making use of the silica of the invention.

In the case where the surfactant must be removed, the method and the silica of the invention remain advantageous over the silicas and methods of the prior art. Indeed, the method and the silica of the invention allow removal of the surfactant by simple washing with water or with a hydroalcoholic solution. The use of a food grade surfactant allows the residual presence of surfactant. When more toxic surfactants are used, it becomes necessary to remove all traces of surfactants, especially for food, medical or even cosmetic applications, and it is then often necessary to perform a calcination step at high temperature which is not necessary, the case for the present invention.

DESCRIPTION OF THE INVENTION

Figure 1:
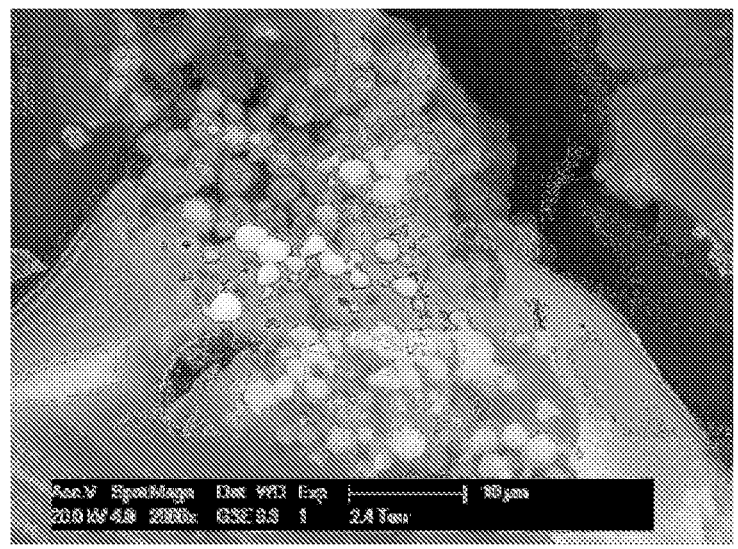
FIG. 1 shows a photograph taken by Philips XL 30 ESEM electron microscope showing particles of silicas.
Figure 2:
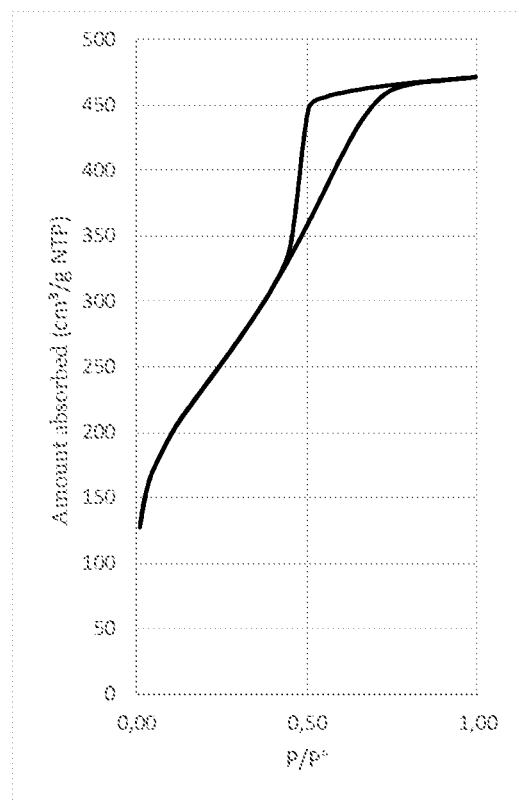
FIG. 2 graph showing the adsorption isotherm of liquid nitrogen at 77K for particles obtained in Example 1.
Figure 3:
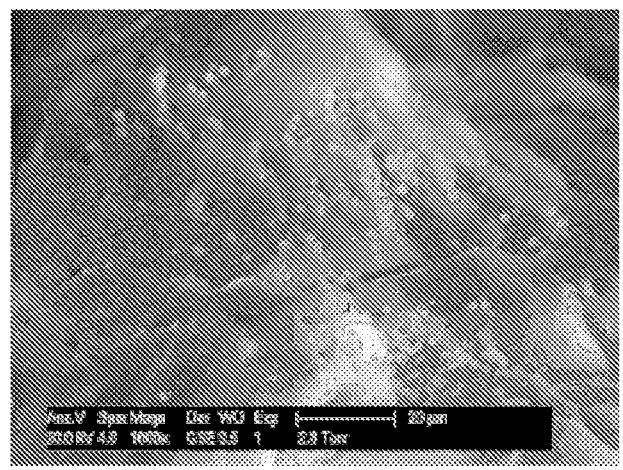
FIG. 3 shows a photograph showing silica particles obtained in Example 2. The photograph was taken by Philips XL 30 ESEM electron microscope.
Figure 4:
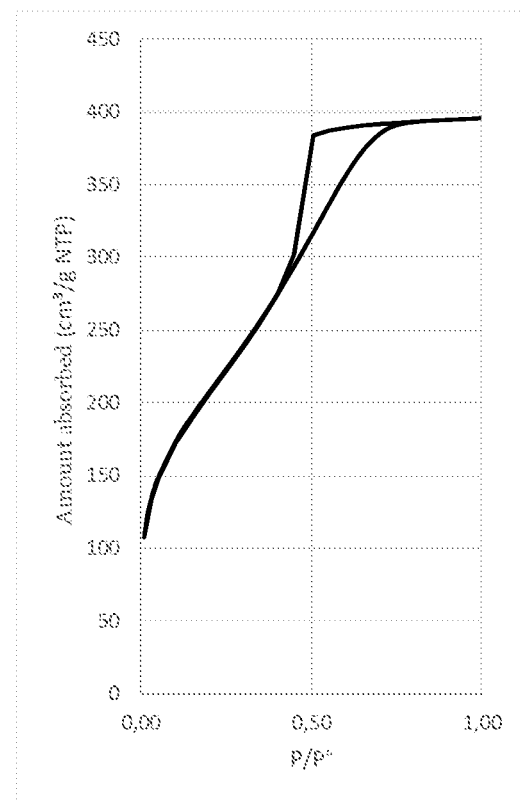
FIG. 4 graph showing the adsorption isotherm of liquid nitrogen at 77K for particles obtained in Example 2.
Figure 5:
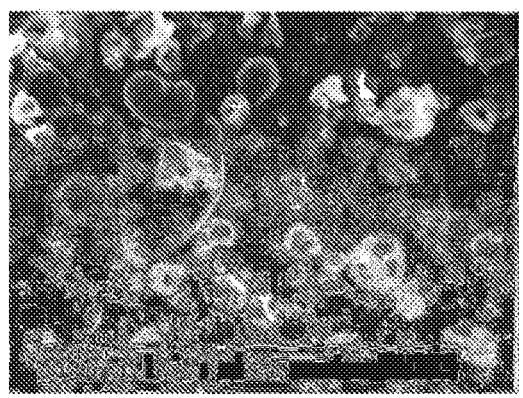
FIG. 5 shows a photograph showing silica particles obtained in Example 3 carried out by Philips XL 30 ESEM electron microscope.
Figure 6:
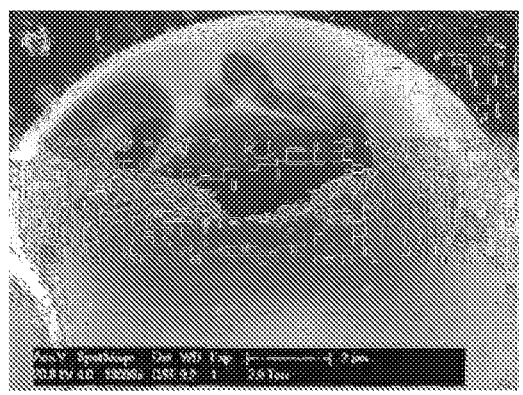
FIG. 6 shows a photograph showing silica particles obtained in Example 3 and in particular the porosity of the particles obtained by electron microscope Philips XL 30 ESEM.
Figure 7:
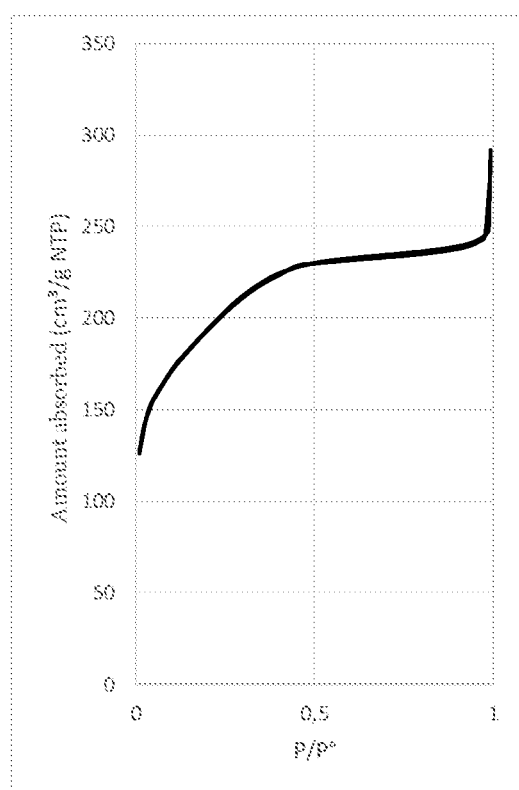
FIG. 7 graph showing the adsorption isotherm of liquid nitrogen at 77K for particles obtained in Example 3.
Figure 8:
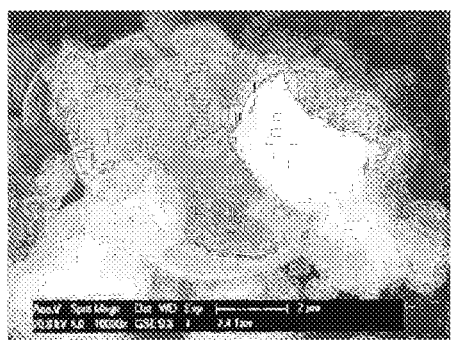
FIG. 8 Photograph showing silica particles obtained in Example 5 carried out by Philips XL 30 ESEM electron microscope.
Figure 9:
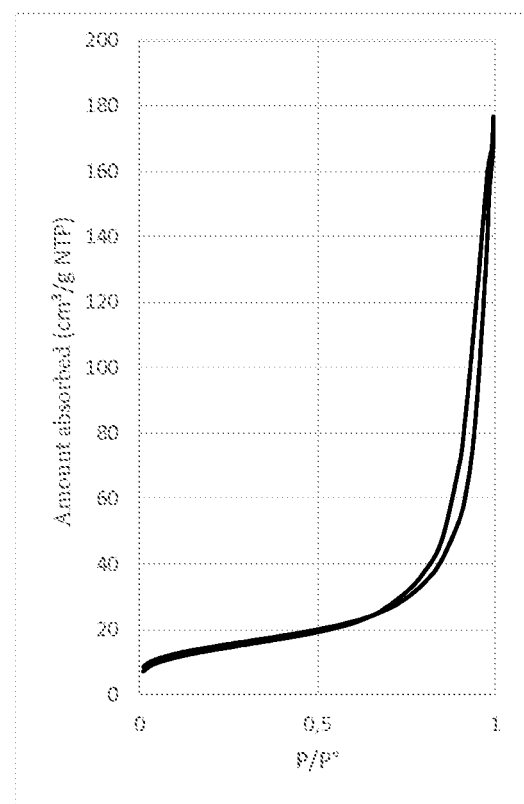
FIG. 9 graph showing the adsorption isotherm of liquid nitrogen at 77K for particles obtained in Example 4.

The present invention relates to a method for the production of mesoporous silica. The method is characterized by the use of at least one natural compound and food grade, including the family of saponins as a structuring agent. The method can be a synthesis in sol-gel or spray drying. The invention also relates to the mesoporous silica obtained through said process.

Unless otherwise stated, all terms used in the disclosure of the invention, including technical and scientific terms, have the meaning as generally understood by those skilled in the art. Term definitions are included to better appreciate the teaching of the present invention.

As used herein, the following terms have the following meanings:

"One", "one", and "the" as used in this document refer to both singular and plural referents unless the context clearly says otherwise. For example, "a compartment" refers to one or more compartments.

"Approximate" as used in this document, refers to a measurable value such as a parameter, a quantity, a time duration, and so on, means to encompass variations of +/− 20% or less, preferably +/− 10% or less, more preferably +/− 5% or less, even more preferably +/− 1% or less and still more preferably +/− 0, 1% or less of and in relation to the specified value as far as such variations are appropriate to function in the disclosed invention. However, it will be appreciated that the value to which the "about" modifier refers is also specifically disclosed.

"Understand", "understand" and "include" and "composed of" as used in this document are synonymous with "include", "include", "include" or "contain", "contains", "contains" and are inclusive or open terms that specify the presence of what follows, for example, a component, and do not exclude or exclude the presence of additional components, features, elements, members, stages, steps, not mentioned, known in the art or revealed within it.

The quotation of numeric ranges by limits includes all the numbers and fractions encompassed in this range, as well as the quoted boundaries.

The mesoporous silica of the invention is also referred to as silica green or green silica.

The terms "structuring agent" and "surfactant" are used as synonyms.

In a first aspect, the present invention provides a mesoporous silica prepared from components A and B such that A is a surfactant of the saponin family and B is a precursor of silica. Silica is obtained by mixing components A and B. The precursor may be soluble or insoluble in water.

In a preferred embodiment, the silica precursor is represented by the formula Si(OR1)(OR2)(OR3)(OR4) in which R1, R2, R3 and R4 are independently selected from hydroxyl, alkyl, glycols, trimethyl-1,2,3,4-tetrahydronaphthalen, 1,1,1,3,3,3-hexafluoropropan-2-yl, dimethylsilyl, trimethylsilyl, ethoxysilyl, tributoxysilyl, diethoxy(methoxy)silyl, trimethoxysilyl, ethoxy(dimethoxy)silyl, butoxy(dipropoxy)silyl, tripropoxysilyl, diethoxy(trimethylsilyloxy)silyl, ethoxy-bis(trimethylsilyloxy)silyl, methylbis(trimethylsilyloxy)silyl, butoxy-bis(trimethylsilyloxy)silyl, diethoxy(triethoxysilyloxy)silyl, dimethyl(vinyl)silyl, trimethylsilyloxy, (3-methylpentoxy)silyl, 4,7,7-trimethyl-3-bicyclo[2.2.1]heptanyl, 2,2,4-trimethyl-3-bicyclo[2.2.1]heptanyl, propan-2-yloxy bis(trimethylsilyloxy)silyl, dibutoxy(trimethylsilyloxy) ilyl, trimethyl trimethoxysilyl, dibutoxy(ethenyl)silyl, diethyl bis(trimethylsilyl), (butan-2-yloxy)silyl, diacetyloxy-[(2-methylpropan-2)-yl)oxy]silyl, acetyloxy(diethoxy)silyl, 4-(dimethylamino)phenyl, 4-(dimethylamino)phenyl, 2-(diethylamino)ethyl, pyridin-3-yl, 2-methylpropan-2-yl)oxy, 2,2,3,3,4,4,5,5,6,6,7,7-dodecafluoroheptyl, trichloro-2-ethylbutoxy, cyclononyl, 1-methoxypropan-2-yl, 2-(2-methoxyethoxy)ethyl, 2-butoxyethyl, 2-ethoxyethyl, 2-methoxyethyl, acetyl, acetyloxy(dipropoxy)silyl, 5-methyl-2-propan-2-ylcyclohexyl, butan-2-yloxy, methylphenyl, cyclohexyl, 2-aminoethyl, phenyl, prop-2-enyl, 2-fluoroethyl, acetate, or trihydroxysilyloxy. The configuration R1=R2=R3=R4 is covered by the invention.

The alkyl groups are preferably selected from methyl and ethyl groups. It is preferred that all O—R bonds be hydrolysable. The preferred silica precursor of formula Si(OR)4 is tetraethyl orthosilicate and/or tetramethyl orthosilicate. According to one embodiment of the invention, the silica precursor is represented by the formula xSiO2:MyO where M is one or more metal atoms, one or more transition metal atoms, one or more non-metal atoms, a methylammonium, actinide, y=1 or 2 or 3 or 4 and x is the SiO2/MyO molar ratio. The metal atom can be alkaline in (y=2) or alkaline earth (y=1). The silica precursor of formula xSiO2:MyO may be chosen from the group comprising orthosilicate, sodium, potassium or calcium metasilicate.

In a preferred embodiment, the structuring agent belongs to the family of saponins. Saponins are amphiphilic molecules naturally produced by certain plants or animals and having surfactant properties. The most important sources of saponins used in the food and cosmetics industry are the *Quillaja saponaria* Molina tree, the *Yucca schidigera*, and the Southeast Asian shrub *Camellia sinensis*, known as the tea plant.

The inventors have discovered that the cooperative self-assembly mechanism can be achieved in the presence of natural saponin-type surfactants. It appears that, as in the case of "conventional" industrial surfactants, the saponins aggregate to form, with the silica precursor, a hybrid phase on which the synthesis of mesoporous material will occur.

The saponins used in the context of this invention are triterpenoid glycosides whose main structure (I) aglycone (sapogenin) can take the following forms: dammarenediols (dammaranes), cucurbitadienol (cucurbitanes), hopanol (hopanes), lanosterols (lanostanes), tirucalladienol (tirucallanes), β-amyrin (oleananes), oo-amyrin (ursanes), taraxasterols (taraxasteranes), lupeol (lupans).

Methyl radicals, carboxylic functions, aldehyde or alcohol; hydrogen atoms, hydroxyl groups; as well as simple or branched osidic chains are also attached to the aglycone backbone. Within the osidic chains, the following sugars are preferred: D-glucose, L-rhamnose, D-galactose, D-glucuronic acid, L-arabinose, D-xylose, D-fructose, D-adipose, D-fucose. In the case where the aglycone comprises an osidic chain, one will speak of monodesmoside and in the case where two chains of glycosides are linked to the skeleton aglycone one will speak of bidesmoside.

In a preferred embodiment, the saponin used has the following oleanane structure such that R1 and R4 are methyl groups, R2 is a hydrogen atom and R3 is a carboxylic group.

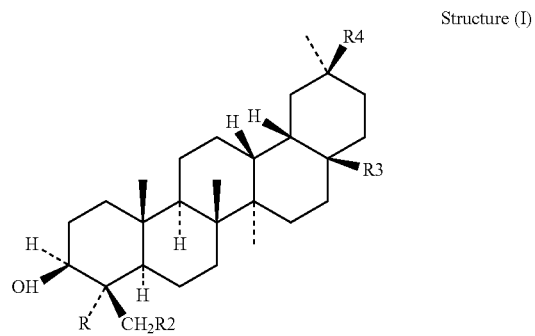

Structure (I)

According to another advantageous embodiment, the structuring agent contains one or more of the following saponins: saponin 1, saponin 2, saponin 3, saponin 4, saponin 5, saponin 6, saponin 6, saponin 7, saponin 8, saponin 9, saponin 10, saponin 19, saponin 20a, saponin 20b, saponin 21a, saponin 21b, saponin 22a, saponin 22b, saponin 23, saponin S7, saponin S8, saponin S9, saponin S10, saponin SU, saponin S12, Quillaja saponin 7, 17, 18 21 (also referred to as QA-7, QA-17, QA-18, QA-21).

According to one embodiment of the invention, the saponins used have a main steroidal aglycone structure of spirostanol or furostanol type or a steroidal glycoalkaloid structure of spirosolane or solanidane type.

In a preferred embodiment, the mesoporous silica of the invention comprises at most 30% by weight of structuring agent relative to the weight of the solid, preferably between 1 and 20% and more advantageously between 1 and 5% by weight of solid. structuring agent with respect to the solid. Said weight of the solid refers to the sum of the weight of the silica and the structuring agent.

In a preferred embodiment, the silica comprises mesopores whose minimum average diameter is 1 nm. The pore diameter was calculated from nitrogen sorption isotherms at liquid nitrogen temperature (77K) according to the method of Barrett, Joyner and Halenda (BJH). The diameter of the mesopores of silica, established from the isotherm of nitrogen sorption at 77K, is 2, 3, 4, 5, 6, 7, 8, 9, 10, 11, 12, 13, 14, 15, 16, 17, 18, 19, 20, 21, 22, 23, 24 or 25 nm or any value between the above values.

In a preferred embodiment, the silica surface area, calculated from nitrogen sorption isotherms at liquid nitrogen temperature (77K) by the Brunauer, Emmett and Teller (BET) theory, is at least 20 m$^2$/g, 40 m$^2$/g, 50 m$^2$/g, or 60 m$^2$/g. The specific surface is at most 800 m$^2$/g, 900 m$^2$/g, 1000 m$^2$/g or 1500 m$^2$/g or any value between the aforementioned values.

In a preferred embodiment, the pore volume of the silica was calculated from nitrogen sorption isotherms at liquid nitrogen temperature (77K) by the method of Barrett, Joyner and Halenda (BJH). Said pore volume is at least 0.1 cm$^3$/g, 0.2 cm$^3$/g, 0.4 cm$^3$/g, 0.5 cm$^3$/g and at most 0.6 cm$^3$/g, 0.8 cm$^3$/g, 1 cm$^3$/g, 1.2 cm$^3$/g, 1.5 cm$^3$/g or any value included between the above values.

In a second aspect, the present invention provides a method of producing mesoporous silica in which components A and B are mixed in a solvent comprising water, such that A is a natural surfactant of the saponin family and B is a precursor of silica. Components A and B are as previously described. The production method is carried out from a micellar solution of surfactant in a solvent comprising water in which the source of silica is added. Said source of silica is preferably added dropwise. Preferably, the solvent is water or a hydroalcoholic solution. The surfactant is as described above.

In a preferred embodiment, the silica precursor is represented by the formula Si(OR)4 where R is an alkyl group, or by the formula xSiO2:MyO where M is a metal atom, y=1 or 2 and x is the SiO2/MyO molar ratio. The silica precursor is as previously described.

In a preferred embodiment, the surfactant is added to the solvent in an amount sufficient to obtain a micellar concentration of between 0.1 and 1000 times the critical micelle concentration. Preferably, the surfactant is added to the solvent in an amount sufficient to obtain a micellar concentration of between 10 and 900 times, 20 and 800 times, 30 and 700 times, 40 and 600 times, 50 and 500 times, 60 and 400 times, and 300 times, 80 and 200 times, 90 and 100 times the critical micellar concentration or all values between the aforementioned values.

In a preferred embodiment, the silica precursor is added to the solvent in an amount sufficient so that the ratio between the amount of silica precursor and the amount of structuring agent is between 0.1 and 50. The silica precursor is preferably added dropwise to the solvent.

In a preferred embodiment, the temperature of the solution obtained following the addition of the silica precursor to the solvent is maintained between 15 and 35° C., preferably between 20 and 25° C. The pH of the surfactant solution is at most 7. The solution can have an acidic pH which is obtained by the addition of suitable solutions and/or molecules such as HCl. The pH of the solvent may be 0, 1, 2, 3, 4, 5, 6, 7 or any value between the above values. The pH of the solvent is preferably 1.

In a preferred embodiment, the mixture is left at rest for at least 5 hours and at most 24 hours at a minimum temperature of 20° C., the rest is followed by a filtration step allowing a solid product to be obtained a. The mixture can also be stirred for at least 10 minutes at a minimum temperature of 20° C., stirring is followed by evaporation of the mixture thus obtaining a solid product b. The product a and/or the product b is then subjected to at least one washing with a solution of ethanol, water or an aqueous-alcoholic solution at atmospheric pressure. The washed product is then subjected to at least one drying step under reduced pressure of 0.1 to 20 mm Hg.

In a preferred embodiment, the method for producing the mesoporous silica comprises the following steps:

The introduction of saponins into acidified water in an amount necessary and sufficient to obtain a micellar concentration of between 0.1 and 1000, preferably between 1 and 1000 times the CMC;

Dissolving the saponins by maintaining the solution at a temperature between 15 and 35° C.;

The dropwise addition of a silica precursor such that the ratio between the amount of silica precursor and the amount of structuring agent is between 0.5 and 50, preferably between 1 and 50;

Aging of the mixture without stirring for a period of time ranging from 10 to 100 hours and preferably from 10 to 20 hours at a temperature of between 20 and 70° C.;

Filtration of the aging product on Büchner;

Carrying out successive washes at atmospheric pressure and at controlled temperature with a 40% vol ethanol solution; and Drying the product under reduced pressure.

In a preferred embodiment, the method of producing the mesoporous silica comprises the following steps:

The introduction of saponins in acidified water or not into a volume necessary and sufficient to obtain a micellar concentration of between 0.1 and 1000, preferably between 1 and 1000 times the CMC;

Dissolving the saponins by maintaining the solution at a temperature between 15 and 35° C.;

The dropwise addition of a silica precursor such that the ratio between the amount of silica precursor and the amount of structuring agent is between 0.5 and 50, preferably between 1 and 50;

Aging of the mixture with or without stirring, for 30 minutes to 72 hours at a temperature of between 20 and 30° C.;

The implementation of aerosol evaporation. The precursor-surfactant mixture is aspirated at the spray dryer and is pushed through a two-fluid or ultrasonic nozzle having an orifice of 0.15 to 1.2 mm to generate droplets of about 20 m. The column inlet temperature is between 120 and 250° C. and preferably between 140 and 180° C. A flow of air with a power of less than 1 m$^3$/min with a suitable temperature at the top of the column allow, 1) the evaporation of the aqueous solvent, 2) the self-assembly of the micelles of surfactant and 3) the condensation of the silica precursor.

The resulting powder, whitish, is washed as described above.

The method of the invention makes it possible to obtain high yields of the order of 60 to 90% relative to the expected mass of solid. Said mass refers to the sum of the mass of the silica and the structuring agent.

The method for synthesizing mesoporous silica according to the invention is characterized by mixing and reacting a silica precursor and a natural structuring agent. The invention is also characterized in that, in view of the chemical and biological properties of the structuring agent, its elimination is made optional. Advantageously, the structuring agent is not eliminated, which makes it possible to accelerate the industrial process and to reduce the cost of industrialization.

In the case where the elimination of the structuring agent and therefore of the saponin is envisaged or required, it can be removed by washing with subcritical water or by successive washing with water or with a water/water mixture, ethanol 40% vol without necessarily using a calcination step. The extracted saponin could be used for the production of other mesoporous silicas and/or for other applications known to those skilled in the art.

EXAMPLES

Example 1

12 N hydrochloric acid is added to 115 ml of water so that the pH is between 1 and 2. An amount of saponin (ABCR) to obtain 10 times the critical micelle concentration is dissolved with stirring at 25° C. in this volume of acidified water. An amount of tetraethoxysilane to obtain a precursor/structure ratio of 50 is then added with stirring dropwise at 0.3 grams per minute. The mixture obtained has a pH of between 1 and 2. The mixture is aged without stirring for 16 hours at 65° C. The gel obtained is filtered on Büchner, washed several times with a 40% vol ethanol solution before being dried under reduced pressure at 40° C. The powder obtained is white. The recovered "green" mesoporous silica has a specific surface area determined by the BET method of 850 $m^2g$-1, a pore volume of 0.7 $cm^3g$-1 and mesopores of 35 Å. The shape of the particles obtained includes spheres and blocks of silicas (FIG. 1 taken by electron microscope PHILIPS XL 30 ESEM).

Example 2

1.5 g of the mesoporous silica obtained according to Example 1 were calcined at 500° C. for 4 hours. The powder obtained is white. The mesoporous silica has a surface area of 750 $m^2g$-1, a pore volume of 0.6 $cm^3g$-1 and mesopores of 32 Å.

Example 3

An amount of saponin (Q-Naturale 200-Desert King) having a triterpene saponin content of 67 to 73% (dry weight) is dissolved with stirring at 25° C. in a volume of acidified water to obtain a corresponding concentration at 10 times the critical micellar concentration. An amount of tetraethoxysilane to obtain a precursor/structure ratio of 10 is then added with stirring dropwise at 0.3 grams per minute. The mixture obtained has a pH of between 1 and 2. The mixture is aged without stirring for 12 to 16 hours at room temperature. The soil thus obtained is introduced into a spray dryer (ProCept R&D spray dryer-Belgium) and sprayed through a nozzle two fluids having an orifice of 0.4 mm under a compressed air pressure of 6 bar. The amount of solution to be atomized is 200 ml. The operating conditions of the spray dryer are as follows:

The incoming air temperature is set at 180° C.
The column outlet temperature is 60° C.
The atomization speed is 7 L·min-1

2.24 grams of white powder of mesoporous silica having a very low bulk density are collected.

The powder obtained is observed by electron microscopy and the analysis shows the presence of cup-shaped particles which is characteristic of spray drying syntheses (Waldron K et al., Formation of monodisperse mesoporous silica microparticles via spray drying. *Journal of Colloid and Interface Science* 418 (2014) 225-233). The synthesized material has a specific surface area of 648 $m^2g$-1, a pore volume of 0.38 $cm^3g$-1 and mesopores of 3.2 nm. FIG. 5, recorded from a PHILIPS XL 30 ESEM electron microscope, shows the shape of the particles obtained. An image showing the porosity is shown in FIG. 6 recorded from a PHILIPS XL 30 ESEM electron microscope.

Example 4

An amount of saponin (Q-Naturale 200-Desert King) having a triterpene saponin content of 67 to 73% (dry weight) is dissolved with stirring at 25° C. in a volume of acidified water to obtain a corresponding concentration at 10 times the critical micellar concentration. An amount of potassium metasilicate to obtain a precursor/structure ratio of 10 is then added with stirring dropwise at 0.3 grams per minute. The mixture obtained has a pH of between 1 and 2. The mixture is aged without stirring for 12 to 16 hours at room temperature. The soil thus obtained is introduced into a spray dryer (ProCept R&D spray dryer-Belgium) and sprayed through a nozzle two fluids having an orifice of 0.4 mm under a compressed air pressure of 6 bar. The amount of solution to be atomized is 200 ml. The operating conditions of the spray dryer are as follows:

The incoming air temperature is set at 180° C.
The column outlet temperature is 60° C.
The atomization speed is 7 L·min-1
3.19 gr of white mesoporous silica powder with a very low apparent density are collected.

The white powder obtained is washed with water and then observed by electron microscopy on a Philips XL30 ESEM microscope. The analysis shows the presence of spherical particles as well as particles of less well-defined shape.

The synthesized material has a specific surface area of 50 $m^2g$-1, a pore volume of 0.23 $cm^3g$-1, and mesopores of 19 nm.

The invention claimed is:

1. A mesoporous silica comprising of a component A and a component B, wherein said component A is a surfactant of a saponin family consisting of *Quillaja Saponaria Molina* tree, *Yucca schidigera* and tea plant, wherein said component B is a precursor of a silica, and wherein said precursor of the silica comprises between 1% and 30% by weight of the surfactant of the saponin family.

2. The mesoporous silica according to claim 1 wherein the precursor of the silica is represented by the formula Si(OR1)(OR2)(OR3)(OR4) wherein R1, R2, R3 and R4 are independently selected from alkyl, hydroxyl, glycols, trimethyl-1,2,3,4-tetrahydronaphthalen, 1,1,1,3,3,3-hexafluoropropan-2-yl, dimethylsilyl, trimethylsilyl, ethoxysilyl, tributoxysilyl, diethoxy(methoxy)silyl, trimethoxysilyl, ethoxy(dimethoxy)silyl, butoxy(dipropoxy)silyl, tripropoxysilyl, diethoxy(trimethylsilyloxy)silyl, ethoxybis(trimethylsilyloxy)silyl, methylbis (trimethylsilyloxy)silyl, butoxybis(trimethylsilyloxy)silyl, diethoxy (triethoxysilyloxy)silyl, dimethyl(vinyl)silyl, trimethylsilyloxy, (3-methylpentoxy) silyl, 4,7,7-trimethyl-3-bicyclo [2.2.1] heptanyl, 2,2,4-trimethyl-3-bicyclo[2.2.1] heptanyl, propanol2-yloxy-bis(trimethylsilyloxy)silyl, dibutoxy (trimethylsilyloxy) silyl, trimethyl trimethoxysilyl, dibutoxy (ethenyl) silyl, diethyl bis(trimethylsilyl), (butan-2-yloxy)silyl, diacetyloxy-[(2-methylpropan-2-yl)oxy]silyl, acetyloxy(diethoxy)silyl, 4-(dimethylamino)phenyl, 4-(dimethylamino)phenyl, 2-(diethylamino)ethyl, pyridin-3-yl, 2 2-methylpropan-2-yl)oxy, 2,2,3,3,4,4,5,5,6,6,7,7-dodecafluoroheptyl, trichloro-2-ethylbutoxy, cyclononyl, 1-methoxypropan-2-yl, 2-(2-methoxyethoxy)ethyl, 2-butoxyethyl, 2-ethoxyethyl, 2-methoxyethyl, acetyl, acetyloxy (dipropoxy)silyl, 5-methyl-2-propan-2-ylcyclohexyl, butan-2-yloxy, methylphenyl, cyclohexyl, 2-aminoethyl, phenyl, prop-2-enyl, 2-fluoroethyl, acetate, or trihydroxysilyloxy or by the formula xSiO2:MyO where M is one or more metal atoms, one or more transition metal atoms, one or non-metal atoms, methylammonium, actinide, y=1 or 2 or 3 or 4 and x is the SiO2/MyO molar ratio.

3. The mesoporous silica according to claim 2 wherein the alkyl is selected from group consisting of methyl and ethyl.

4. The mesoporous silica according to claim 1 wherein the mesoporous silica comprises mesopores having an average diameter of at least 1 nm.

5. The mesoporous silica according to claim 1, wherein the mesoporous silica has a specific surface area, measured by a BET method, of at least 20 m$^2$/g.

6. The mesoporous silica according to claim 1 wherein the mesoporous silica has a pore volume of at least 0.1 cm$^3$/g.

7. A method of producing a mesoporous silica comprising: mixing a component A and a component B in a solvent, wherein said solvent comprising water, wherein said component A is a surfactant of a saponin family consisting of *Quillaja saponaria* Molina tree, *Yucca schidigera* and tea plant, and wherein said component B is a precursor of a silica.

8. The method according to claim 7 wherein the precursor of the silica is represented by the formula Si(OR1)(OR2)(OR3)(OR4) wherein R1, R2, R3 and R4 are independently selected from alkyl, hydroxyl, glycols, trimethyl groups 1,2,3,4-tetrahydronaphthalen, 1,1,1,3,3,3-hexafluoropropan-2-yl, dimethylsilyl, trimethylsilyl, ethoxysilyl, tributoxysilyl, diethoxy(methoxy)silyl, trimethoxysilyl, ethoxy(dimethoxy)silyl, butoxy(dipropoxy)silyl, tripropoxysilyl, diethoxy(trimethylsilyloxy)silyl, ethoxy-bis(trimethylsilyloxy)silyl, methylbis(trimethylsilyloxy)silyl, butoxy-bis(trimethylsilyloxy)silyl, diethoxy(triethoxysilyloxy)silyl, dimethyl(vinyl)silyl, trimethylsilyloxy, (3-methylpentoxy)silyl, 4,7,7-trimethyl-3-bicyclo[2.2.1]heptanyl, 2,2,4-trimethyl-3-bicyclo[2.2.1]heptanyl, propan-2-yloxy-bis(trimethylsilyloxy)silyl, dibutoxy (trimethylsilyloxy) silyl, trimethyl trimethoxysilyl, dibutoxy (ethenyl) silyl, diethyl bis(trimethylsilyl), (butan-2-yloxy)silyl, diacetyloxy-[(2-methyl)propan-2-yl)oxy]silyl, acetyloxy(diethoxy)silyl, 4-(dimethylamino)phenyl, 4-(dimethylamino)phenyl, 2-(diethylamino)ethyl, pyridin-3-yl, 2-methylpropan-2-yl)oxy, 2,2,3,3,4,4,5,5,6,6,7,7-dodecafluoroheptyl, trichloro-2-ethylbutoxy, cyclononyl, 1-methoxypropan-2-yl, 2-(2-)methoxyethoxy)ethyl, 2-butoxyethyl, 2-ethoxyethyl, 2-methoxyethyl, acetyl, acetyloxy(dipropoxy)silyl, 5-methyl-2-propan-2-ylcyclohexyl, butan-2-yloxy, methylphenyl, cyclohexyl, 2-aminoethyl, phenyl, prop-2-enyl, 2-fluoroethyl, acetate, or trihydroxysilyloxy or by the formula xSiO2:MyO where M is one or more metal atoms, one or more transition metal atoms, one or more non-metal atoms, a methylammonium, an actinide, y=1 or 2 or 3 or 4 and x is the SiO2/MyO molar ratio.

9. The method of claim 7 wherein the precursor of the silica is added to the solvent dropwise.

10. The method of claim 7 wherein the solvent has a temperature maintained between 15 and 35° C.

11. The method according to claim 7 wherein the solvent has a pH of at most 7.

12. The method according to claim 7 further comprising aging the mixture for at least 5 hours at a minimum temperature of 20° C. followed by a filtration step for obtaining a solid product a.

13. The method according to claim 7 further comprising stirring the mixture for at least 10 min at a minimum temperature of 20° C. followed by evaporation and/or aspiration of the mixture for obtaining a solid product b.

14. The method according to claim 12 further comprising washing the solid product a with an ethanol solution at atmospheric pressure.

15. The method according to claim 14 further comprising drying the solid product a under reduced pressure of 0.1 to 20 mm Hg.

16. The method according to claim 13 further comprising washing the solid product b with an ethanol solution at atmospheric pressure.

17. The method according to claim 16 further comprising drying the solid product b under reduced pressure of 0.1 to 20 mm Hg.

* * * * *